US012557971B2

(12) United States Patent
Park et al.

(10) Patent No.: US 12,557,971 B2
(45) Date of Patent: Feb. 24, 2026

(54) DETACHABLE ENDOSCOPE FOR THE DUODENUM

(71) Applicant: TAEWOONG MEDICAL CO., LTD., Gimpo-si (KR)

(72) Inventors: Sung Hwan Park, Seoul (KR); Hyun Soo Ji, Seoul (KR)

(73) Assignee: TAEWOONG MEDICAL CO., LTD., Gimpo-si (KR)

( * ) Notice: Subject to any disclaimer, the term of this patent is extended or adjusted under 35 U.S.C. 154(b) by 384 days.

(21) Appl. No.: 18/155,371

(22) Filed: Mar. 2, 2023

(65) Prior Publication Data

US 2023/0225588 A1     Jul. 20, 2023

(30) Foreign Application Priority Data

Jan. 14, 2022     (KR) ........................ 10-2022-0006185

(51) Int. Cl.
*A61B 1/00*          (2006.01)
*A61B 1/005*         (2006.01)

(52) U.S. Cl.
CPC ........ *A61B 1/00105* (2013.01); *A61B 1/0057* (2013.01)

(58) Field of Classification Search
CPC .......................... A61B 1/00105; A61B 1/0057
See application file for complete search history.

(56)                References Cited

U.S. PATENT DOCUMENTS

| | | | | |
|---|---|---|---|---|
| 2006/0287576 A1* | 12/2006 | Tsuji | .................. | A61B 1/00105 600/132 |
| 2012/0004503 A1* | 1/2012 | Kawaura | ............ | A61B 1/00128 600/104 |

| | | | | |
|---|---|---|---|---|
| 2019/0313881 A1* | 10/2019 | Francher | ............ | A61B 1/00052 |
| 2020/0367732 A1* | 11/2020 | Yamaya | ............. | A61B 1/00098 |
| 2021/0068621 A1* | 3/2021 | Shin | .................... | A61B 1/00073 |
| 2022/0265967 A1* | 8/2022 | Alhadeff | .......... | A61M 25/0136 |

FOREIGN PATENT DOCUMENTS

| | | |
|---|---|---|
| CN | 111493795 A | 8/2020 |
| JP | S5937922 A | 3/1984 |
| JP | H07-184848 A | 7/1995 |
| JP | 2003-190078 A | 7/2003 |
| JP | 2004-321822 A | 11/2004 |
| JP | 2021-041155 A | 3/2021 |

OTHER PUBLICATIONS

Isamu Watanabe, "Office Action for Japanese Application 2023-003682", Jan. 9, 2024, JPO, Japan.

* cited by examiner

*Primary Examiner* — Michael J Carey
*Assistant Examiner* — Olivia Grace Starkey
(74) *Attorney, Agent, or Firm* — Bridgeway IP Law Group, PLLC; Jihun Kim

(57)                ABSTRACT

A detachable endoscope for a duodenum including an insertion unit whose one end is intended to be inserted into a body, and which is provided with a force applying module pivotably disposed on the one end; an operation unit coupled to another end of the insertion unit, and operating the one end of the insertion unit to perform a bending motion with use of an operation module; and a detachment unit including a first detachment module disposed within the operation unit, and a second detachment module disposed within the insertion unit and detachably coupled to the first detachment module.

5 Claims, 8 Drawing Sheets

10

200    300    100    H

200a

Z
Y    X

DETACHABLE ENDOSCOPE FOR THE DUODENUM

BACKGROUND OF THE INVENTION

Field of the Invention

The present disclosure relates to a device, and more particularly to a detachable endoscope for the duodenum.

Background Art

In general, a medical procedure using an endoscope is to insert an endoscope equipped with a camera and a medical procedure tool through a small hole without making a large incision in the body of a patient, and then proceed with the procedure while observing the affected part of the patient through the image taken by the endoscope in the body. In particular, the endoscopic procedure starting from laparoscopic surgery has advantages in that the incision region is smaller than that of laparotomy, so the scar region is also small, and there is little bleeding, which leads to the quick patient recovery after the procedure.

The conventional endoscopes are integrally constituted with an insertion part intended to be inserted into the human body and an operation part that operates the insertion part, and a plurality of channels and guides are embedded through the inside of each part. In particular, an image sensing device such as an expensive CCD is provided at the front end of the insertion part inserted into the body. Therefore, it is difficult to separate only the insertion part from the operation part and replace it with a new one. To overcome this problem, in line with the trend of strengthening the sanitary function of medical endoscopes, various types of detachable endoscopes are being used in which an insertion part intended to be inserted into the body and an operation part for operating the insertion part are connected to each other when being used, or separated from each other when being stored.

However, in the conventional detachable endoscope having a structure in which the operation part and the insertion part are detachably coupled by the medium of the connection part, in order to separate the insertion part and the operation part from each other by releasing the engagement in the connection part after the endoscopic procedure, a pressing member such as a button must be provided in the connection part, and the engagement connection in the connection part must be released using this pressing member. Therefore, the structure of the connection part that detachably connects the operation part and the insertion part to each other becomes very complicated, and the manufacturing cost of the endoscope increases.

Further, the overall number of components provided in the connection part of the endoscope increases due to the engagement release button and accessory structures associated therewith additionally provided in the connection part. In the case of a mechanical malfunction of the engagement release button, the endoscope for a medical procedure cannot be used, while the cost required to maintain/repair the connection part increases.

SUMMARY OF THE INVENTION

A technical problem to be addressed by the present disclosure is to provide a detachable endoscope that prevents internal contamination of the endoscope and allows easy replacement and cleaning of a part intended to be inserted into the human body by configuring the detachable endoscope such that the part is detachable.

Technical drawbacks, which the present disclosure is to address, are limited to the aforementioned ones, and unmentioned or other technical drawbacks may be clearly appreciated from the following detailed description by a person having ordinary skill in the art to which the present disclosure belongs.

To accomplish the above-described technical objects, a detachable endoscope for a duodenum according to an example of this disclosure may include an insertion unit whose one end is intended to be inserted into a body, and which is provided with a force applying module pivotably disposed on the one end; an operation unit coupled to another end of the insertion unit, and operating the one end of the insertion unit to perform a bending motion with use of an operation module; and a detachment unit including a first detachment module disposed within the operation unit, and a second detachment module disposed within the insertion unit and detachably coupled to the first detachment module.

According to an example of this disclosure, the first detachment module may include a first module body, and a first intermediate connection part and a second intermediate connection part disposed within the first module body and receiving a force from the operation module, and the second detachment module may include a second module body, and a first insertion end connection part and a second insertion end connection part disposed within the second module body, detachably connected to the first intermediate connection part, and respectively connected to a first operation wire and a second operation wire transferring a force applied by the operation module to one end of the insertion module or the force applying module.

According to an example of this disclosure, the first intermediate connection part may be provided in two pairs, which are spaced apart from each other along the inner circumference of the first module body, and the second intermediate connection part may extend through the center of the two pairs of the first intermediate connection parts, and the first insertion end connection part may be provided in two pairs corresponding to the first intermediate connection parts, and the two pairs of the first insertion end connection parts may be spaced apart from each other along the inner circumference of the second module body, and the second insertion end connection part may extend through the center of the two pairs of the first insertion end connection parts.

According to an example of this disclosure, each of the first intermediate connection part and the second intermediate connection part may be provided with an insertion groove formed concavely inward in a longitudinal direction at its one end, and each of the first insertion end connection part and the second insertion end connection part may be provided with an engaging member formed protrudingly outward in a longitudinal direction from its one end and detachably inserted into and coupled to the insertion groove.

According to an example of this disclosure, the engaging member may be formed protrudingly in a length shorter than the concave depth of the insertion groove.

According to an example of this disclosure, the second insertion end connection part may be connected to the force applying module by a medium of the operation wire, and when the first detachment module and the second detachment module are coupled to each other, the force applying module may be operated to rotate about a rotational axle perpendicular to the longitudinal direction of the insertion unit with use of the operation module.

According to an example of this disclosure, the second insertion end connection part may be provided with a curved connection member extending toward the force applying module and at least partially curved with respect to the longitudinal direction of the second insertion end connection part.

In the detachable endoscope according to the embodiments of the present disclosure, the insertion unit intended to be inserted into the human body is configured to be detachable from the operation unit, so that the internal contamination of the endoscope can be prevented and parts can be easily replaced and cleaned. Additionally, in the course of coupling, without the use of a separate engaging or locking structure, it is possible to realize simple and easy assembly and disassembly of the insertion unit.

The effects of the present disclosure are not limited to the aforementioned effects, but should be understood as including all effects that can be inferred from the configuration provided by the description or claims of the present application.

BRIEF DESCRIPTION OF THE DRAWINGS

FIG. 8 includes an enlarged perspective view showing the insertion end of the insertion unit.

DETAILED DESCRIPTION OF THE INVENTION

Figure 1:
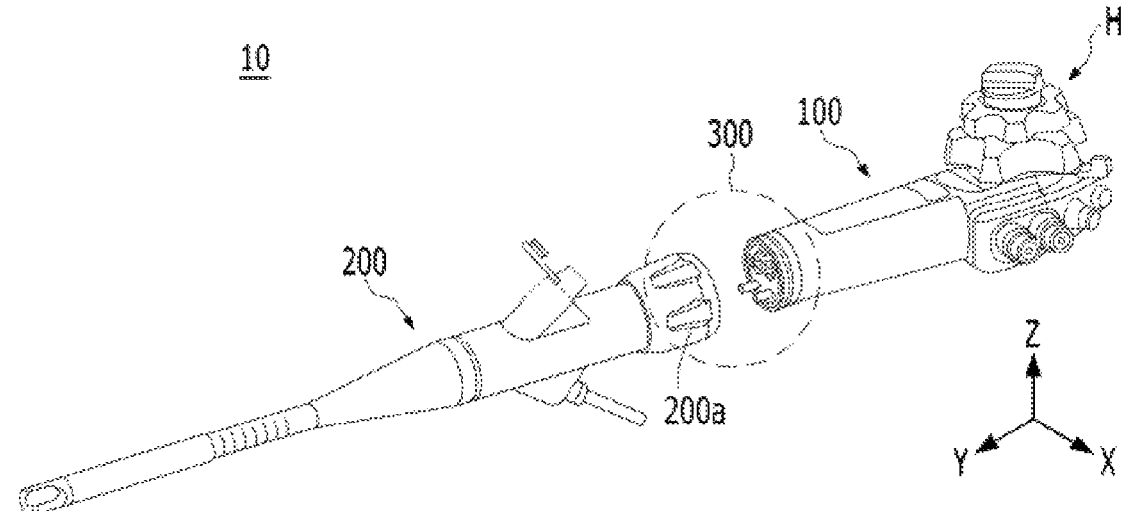
FIG. 1 is a perspective view showing a detachable endoscope according to an embodiment of the present disclosure.

Hereinafter, embodiments of the present disclosure will be described with reference to the accompanying drawings. However, the disclosure can be embodied in various different fors, and the scope of the disclosure should not be construed as being limited to the embodiments described herein. In the drawings, in order to describe clearly the disclosure, parts not related to the description are omitted, and like reference signs will be given to like constitutional elements throughout the specification.

As used herein, "connecting(or combining)" a part with another part (or "bring" a part into contact or touch with another part) may refer to a case where they are "indirectly connected" to each other with other element intervening therebetween, as well as a case where they are "directly connected". Further, when a part "includes(or comprises)" a component, it means not that the part excludes other component, but instead that the part may further include other component unless expressly stated to the contrary.

The terms used herein are used to merely describe specific embodiments, but are not intended to limit the disclosure. Singular expressions may include the meaning of plural expressions unless the context clearly indicates otherwise. The terms such as "include (or comprise)", "have (or be provided with)", and the like are intended to indicate that features, numbers, steps, operations, components, parts, or combinations thereof written in the following description exist, and thus should not be understood as that the possibility of existence or addition of one or more different features, numbers, steps, operations, components, parts, or combinations thereof is excluded in advance.

Hereinafter, embodiments of this disclosure will be described in detail with reference to the accompanying drawings.

Figure 2:
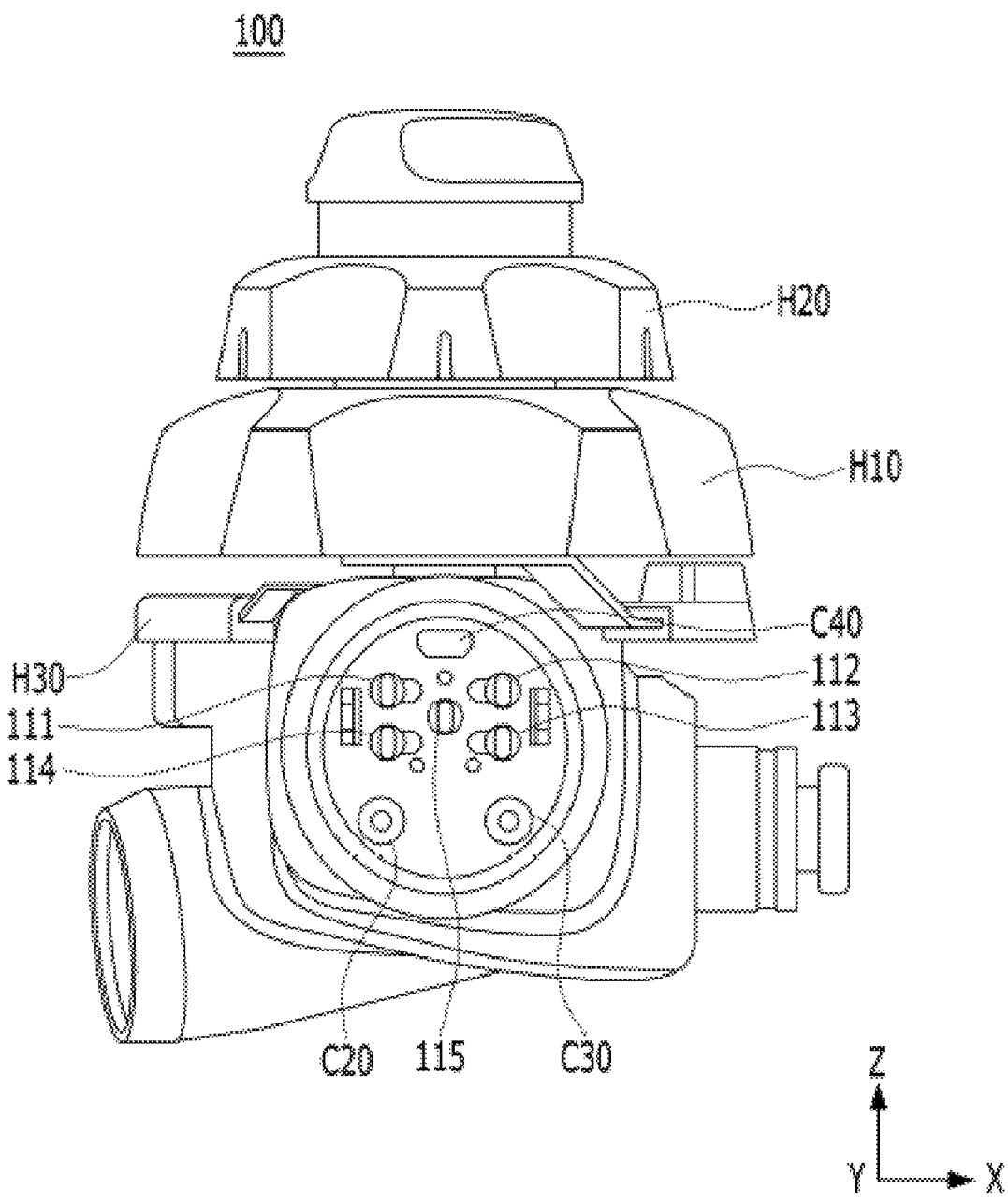
FIG. 2 is a front view showing one end of an operation unit provided in a detachable endoscope according to an embodiment of the present disclosure.
Figure 3:
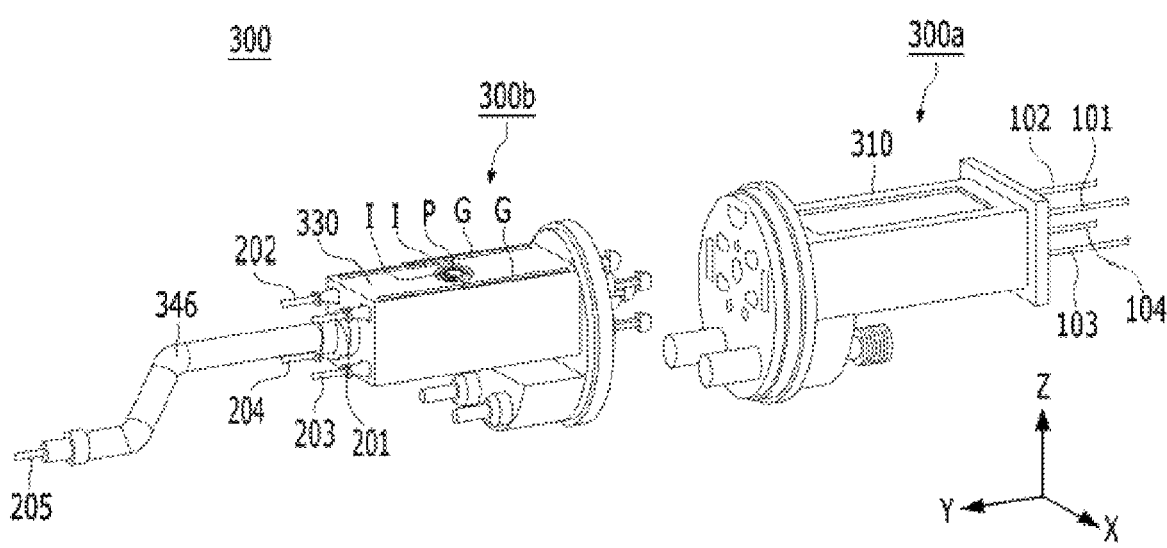
FIG. 3 is a perspective view showing a state before the coupling of a first detachment module and a second detachment module provided in a detachment unit according to an embodiment of the present disclosure.
Figure 4:
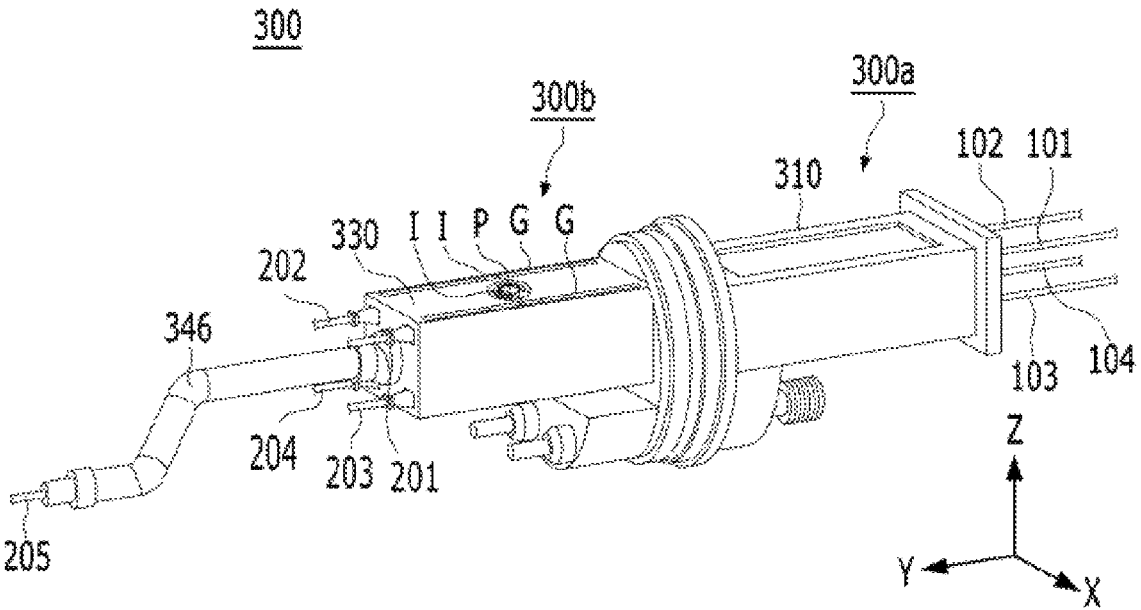
FIG. 4 is a perspective view showing a state in which a first detachment module and a second detachment module provided in a detachment unit according to an embodiment of the present disclosure are coupled to each other.

FIG. 1 is a perspective view showing a detachable endoscope according to an embodiment of the present disclosure. FIG. 2 is a front view showing one end of an operation unit provided in a detachable endoscope according to an embodiment of the present disclosure. FIG. 3 is a perspective view showing a state before the coupling of a first detachment module and a second detachment module provided in a detachment unit according to an embodiment of the present disclosure. FIG. 4 is a perspective view showing a state in which a first detachment module and a second detachment module provided in a detachment unit according to an embodiment of the present disclosure are coupled to each other.

Referring to FIGS. 1 to 4, a detachable endoscope 10 may be a device for inspecting and performing medical procedures on organs inside a body. Here, the target part for the inspection and medical procedure may be, for example, the duodenum.

The detachable endoscope 10 may include an operation unit 100, an insertion unit 200, and a detachment unit 300. In addition, the detachable endoscope 10 may further include a joint unit (not shown) electrically connected to an endoscope control and management system (not shown).

The operation unit 100 is a part that the user manipulates to control the operation of the insertion unit 200, and may include an operation module H. In this case, the operation module H may include a first operation part H10, a second operation part H20, and a third operation part H30.

To one end (hereinafter, a first coupling end) of the operation unit 100, the detachable insertion unit 200 can be selectively connected. In the state in which the insertion unit 200 is coupled to the operation unit 100, the user can rotate the first operation part H10 in left and right directions, so that the front end (hereinafter, referred to as an insertion end) of the insertion unit 200 can be caused to perform a bending motion in up and down directions, or can rotate the second operation part H20 in left and right directions, so that the aforementioned front end can be caused to perform a bending motion in left and right directions. Additionally, the user can control the pivoting of a force applying module 400 to be described later by rotating the third operation part H30 in one direction.

The first operation part H10 may be provided with a lower sprocket (not shown) and a lower chain (not shown) meshed therewith, and the second operation part H20 may be provided with an upper sprocket (not shown) and an upper chain (not shown) meshed therewith. In this case, when the first operation part H10 and/or the second operation part H20 are/is rotated by the user's manipulation, the lower sprocket and/or the upper sprocket rotate(s), and this rotational motion can be converted into reciprocating rectilinear motion by the lower chain and/or the upper chain.

The lower chain and the upper chain may be connected to the inside of the insertion unit 200 by the medium of a first, second, third and fourth connection wires 101, 102, 103 and 104 and a first, second, third and fourth operation wires 201, 202, 203 and 204, which will be described later. In this case, by the reciprocating rectilinear motion of the upper chain and/or the lower chain, the first, second, third, and fourth connection wires 101, 102, 103, 104 and the first, second, third, and fourth operation wires 201, 202, 203, 204 are selectively linearly moved, so that the insertion end of the insertion unit 200 connected to the first, second, third, and fourth operation wires 201, 202, 203, 204 can be bent in the up and down directions or in the left and right directions. At this time, the user can adjust the bending amount of the insertion end by appropriately changing the rotation angle of the first operation part H10 and/or the second operation part H20.

In this case, the rotation of the lower sprocket and the upper sprocket may be made by the manual rotational manipulation of the user who holds the first operation parts H10 and the second operation part H20 provided in the operation module H. However, the present disclosure is not limited to this, but it may also be constituted by connecting a rotational axle connected to each of the lower sprocket and the upper sprocket with a driving means such as an electric motor, and using a separate remote control means for controlling the driving means.

The third operation part H30 may be connected to a lifting unit (not shown) disposed inside the operation unit 100. In this case, the lifting unit may be operated, as an embodiment, in a hydraulic manner. In this case, the lifting unit may include a hydraulic pressure supply part (not shown) and a linear movement shaft (not shown). In this case, the hydraulic pressure supply part may supply hydraulic pressure to the linear movement shaft connected to an intermediate connection member 105 to be described later based on the manipulation of the third operation part H30.

At this time, when the third operation part H30 is rotated in one of the left and right directions (hereinafter, referred to as the operation direction) by the user in a state in which the insertion unit 200 is coupled to the operation unit 100, the linear movement shaft can move backward (−Y axis direction) due to the hydraulic pressure supplied by the hydraulic pressure supply part.

Accordingly, the intermediate connection member 105 and the second intermediate connection body 315, and the second insertion end connection body 345 coupled thereto and the fifth operation wire 205 move in the direction of being pulled toward the operation unit 100 (hereinafter, referred to as the force applying direction) (e.g., −Y axis direction), so that force can be applied to the force applying module 400 connected to the fifth operation wire 205 in the force applying direction (−Y axis direction). Accordingly, the force applying module 400 can pivot in the first rotation direction R1 toward the operation unit 100 around the pivot axis C.

Meanwhile, the present disclosure is not limited to the above-described embodiment, but the lifting unit may also rotate the force applying module 400 by being operated in a manner other than the hydraulic manner. However, for the convenience of description, hereinafter, an embodiment in which the lifting unit operates in a hydraulic manner will be mainly described.

Meanwhile, the third operation part H30 may be provided with an elastic part (not shown). This elastic part may be compressed and deformed as the third operation part H30 is rotated in the operation direction by the user. Thereafter, by generating an elastic restoring force in the opposite direction to the operation direction and returning the third operation part H30 to its original position when the force applied to the third operation unit H30 is removed, the hydraulic pressure applied to the linear movement shaft is removed, so that the second intermediate connection part, the second insertion end connection part, and the fifth operation wire 205 can move back in an opposite direction (Y axis direction) to the force applying direction. Accordingly, the force applying module 400 can rotate in the second rotation direction R2 opposite to the first rotation direction R1, and can return to the original position.

A part (i.e., the insertion end) of the insertion unit 200 may be inserted into the body during an endoscopic procedure. In this case, the insertion end of the insertion unit 200 may be an end among both ends of the insertion unit 200, which is opposite to the end coupled to the operation unit 100 (hereinafter, referred to as a second coupling end). At the insertion end, an illuminating and photographing unit may be provided which has a light source for illuminating the inside of the body, and an image sensor for photographing the inside of the body.

The aforementioned force applying module 400 may be disposed at the insertion end of the insertion unit 200. Specifically, the force applying module 400 may be disposed in the opening provided at the aforementioned insertion end. In this case, the force applying module 400 may be installed to be pivotable around a connection axis C perpendicular to the longitudinal direction (Y axis direction) of the insertion unit 200.

During an endoscopic procedure, a separate procedure equipment may be inserted into the insertion unit 200 through an insertion structure for connection provided in the detachable endoscope 10. This procedure equipment may pass through the inner passage (not shown) of the insertion unit 200, and moves to the outside of the insertion end through the above-mentioned opening to perform a medical procedure on the duodenum or the like.

In this case, the force applying module 400 may apply force to the procedure equipment, which has been moved to the outside of the insertion end through the opening, to bend the procedure equipment toward a position where the medical procedure is required.

For example, during an endoscopic procedure, by rotating the force applying module 400 in the first rotation direction R1 using the third operation unit H30, the procedure equipment can be bent in a direction corresponding to the first rotation direction R1. In the case where the endoscopic procedure is completed or the procedure equipment needs to be replaced, by removing the force applied to the third operation part H30 and returning the force applying module 400 to its original position, it is possible to remove the force applied to the procedure equipment and return it to the state before the bending.

In an example, the insertion unit 200 may have an elongate cylindrical shape with a hollow formed therein. At least this portion of the insertion unit 200 may be formed with a flexible material, so that the bending direction can be adjusted by the operation unit 100 as described above. For example, a cover forming the outer surface of the insertion unit 200 may be formed with a flexible tube material such as a resin composition.

Meanwhile, the operation unit 100 may include a manipulation switch and a manipulation button for injecting or discharging liquid and gas used during an endoscopic procedure. A part (e.g., the second coupling end or its periphery) of the insertion unit 200 detachably coupled with the first coupling end of the operation unit 100 via the detachment unit 300 may be provided with an entrance through which a medical procedure tool such as an endoscopic procedure tool having a clip is protruded from or retracted into the insertion unit 200, and with a cap for opening and closing the entrance.

As exemplarily shown in FIGS. 2 to 4, a first support cover K10 may be provided at the first coupling end of the operation unit 100. In this case, an air supply channel C30 for supplying air, a water supply channel C20 for supplying water, and a terminal C40 electrically connected to an illuminating and photographing part provided at the above-described insertion end may be formed to pass through the first support cover K10.

The detachment unit 300 may detachably connect the operation unit 100 and the insertion unit 200. In this case, the detachment unit 300 may include a first detachment module 300a and a second detachment module 300b that are detachably coupled to each other. The operation unit 100 and the insertion unit 200 may be connected or separated by the coupling or decoupling of the first detachment module 300a and the second detachment module 300b.

The first detachment module 300a may be arranged to be inserted into the operation unit 100, and may include a first module body 310, a first intermediate connection part and a second intermediate connection part. And the second detachment module 300b may be arranged to be inserted into the insertion unit 200, and may be provided with a second module body 330, a first insertion end connection part, and a second insertion end connection part.

In this case, although reference numerals are not indicated in the drawings, for the convenience of description, hereinafter, the first intermediate connection part will be denoted by reference number 320, and the second intermediate connection part will be denoted by reference number 320'. Additionally, the first insertion end connection part will be denoted by reference number 340, and the second insertion end connection part will be denoted by reference number 340'.

The first module body 310 may be a housing in which a first middle hollow and a second middle hollow are formed penetrating both ends along the longitudinal direction (Y axis direction). These first and second middle hollows may be arranged on the same line to be communicated with each other, along the through holes for connection 111, 112, 113, 114, and 115 (in FIG. 2) provided in the first support cover K10 and the longitudinal direction (Y axis direction).

The first intermediate connection part 320 may connect the operation module H and the first insertion end connection part 340 to be described later by the medium of the first, second, third, and fourth connection wires 101, 102, 103, and 104. At this time, the first intermediate connection part 320 may be provided with two pairs of first intermediate connection bodies 311, 312, 313, and 314, and first connection ends E1, E2, E3, and E4 respectively provided thereto.

In an example, the first intermediate connection bodies 311, 312, 313, and 314 may be bars having an elongate cylindrical shape. The first intermediate connection bodies 311, 312, 313, and 314 may be inserted penetrating the first middle hollow of the first module body 310. At this time, both ends of the first intermediate connection bodies 311, 312, 313, and 314 may be disposed at least partially outside the first module body 310.

The first connection ends E1, E2, E3, and E4 may be detachably connected to first engaging members 331, 332, 333, and 334 to be described later. The first connection ends E1, E2, E3, and E4 may be disposed at one ends of the first intermediate connection bodies 311, 312, 313, and 314, and these one ends of the first intermediate connection bodies 311, 312, 313, and 314 may be ends facing the insertion unit 200. The other ends of the first intermediate connection bodies 311, 312, 313, and 314 may be connected to one ends of the first, second, third, and fourth connection wires 101, 102, 103, and 104, and at this time, the other ends of the first, second, third, and fourth connection wires 101, 102, 103, and 104 may be connected to the lower chain or the upper chain provided in the first operation part H10 or the second operation part H20.

In this case, as the user manipulates the first operation part H10 or the second operation part H20, the rotational motion of the lower sprocket or the upper sprocket can be converted into reciprocating rectilinear motion by the lower chain or upper chain, and subsequently, the first, second, third, and fourth connection wires 101, 102, 103, and 104 connected to the lower chain or the upper chain can perform reciprocating rectilinear motion. Accordingly, the first intermediate connection bodies 311, 312, 313, and 314 connected to the first, second, third and fourth connection wires 101, 102, 103, and 104, and the first connection ends E1, E2, E3, and E4 can perform reciprocating rectilinear motion along a direction parallel to the longitudinal direction (Y axis direction).

The first connection ends E1, E2, E3, and E4 may be formed with a larger outer diameter than the outer diameter of the first intermediate connection bodies 311, 312, 313, and 314. At this time, elastic members, which the intermediate connection bodies 311, 312, 313, and 314 are inserted penetrating, may be disposed between the first connection ends E1, E2, E3, and E4 and the first, second, third, and fourth connection wires 101, 102, 103, and 104. As the first intermediate connection bodies 311, 312, 313, and 314 are pressed by the first insertion end connection part 340 during the coupling process, these elastic members are compressed and deformed, and can generate an elastic restoring force for returning the first intermediate connection bodies 311, 312, 313, and 314 to their original positions. The elastic member may be constituted with, for example, a coil spring.

The first coupling ends E1, E2, E3, and E4 may be provided with first insertion grooves 321, 322, 323, and 324 into which the first engaging members 331, 332, 333, and 334 are inserted when the insertion unit 200 and the operation unit 100 are coupled to each other, and first guide projections T1, T2, T3, and T4 for guiding rotation of the first intermediate connection bodies 311, 312, 313, and 314.

The first insertion grooves 321, 322, 323, and 324 may be formed concavely in the longitudinal direction (e.g., −Y axis direction) inward from the first connection ends E1, E2, E3, and E4. The first insertion grooves 321, 322, 323, and 324 may be provided with penetration parts N formed to penetrate through the first connection ends E1, E2, E3, and E4 in a direction (X axis direction) perpendicular to the longitudinal direction (Y axis direction). The first insertion grooves 321, 322, 323, and 324 may be partially communicated with the outside through the penetration parts N. Additionally, the first engaging members 331, 332, 333, and 334 can be in an engaged state and secured in the first insertion grooves 321, 322, 323, and 324 by the penetration parts N.

The first guide projections T1, T2, T3, and T4 can guide the rotational motion of the first intermediate connection bodies 311, 312, 313, and 314. The first guide projections T1, T2, T3, and T4 may be formed to protrude toward the outside in the radial direction from the first connection ends E1, E2, E3, and E4 of the first intermediate connection bodies 311, 312, 313, and 314.

In the case where after the insertion of the first engaging members 331, 332, 333, and 334 into the first insertion grooves 321, 322, 323, and 324, the first insertion end connection bodies 341, 342, 343, and 344 press the first connection ends E1, E2, E3, and E4, or the second insertion end connection part 340' is pulled and moved backward (−Y axis direction) by the manipulation of the operation module H, the first guide projections T1, T2, T3, and T4 can move along the first guide slits G1, G2, G3, and G4 formed in the first module body 310.

The first guide slits G1, G2, G3, and G4 may include a curved line part that is curved and extended from one side of the first module body 310 to the other side thereof, and a straight line part connected to this curved line part and extending backward (−Y axis direction) parallel to the longitudinal direction of the first intermediate connection bodies 311, 312, 313, and 314.

In the case where the first insertion end connection part 340 moves backward (−Y axis direction), the first guide projections T1, T2, T3, and T4 first rotate along the curved line part, and thereby the first intermediate connection body 311, 312, 313, and 314 can be rotated and simultaneously guided to move backward (−Y axis direction) by the first guide projection T1, T2, T3, and T4. Thereafter, as the first insertion end connection part 340 moves further backward (−Y axis direction), the guide projections T1, T2, T3, and T4 passing through the curved line part move linearly along the straight line part, and accordingly, the first engaging members 331, 332, 333, and 334 are engaged inside the first insertion grooves 321, 322, 323, and 324, and thereby the first intermediate connection part 320 and the second insertion end connection part 340' are coupled so that they are not separated during the endoscopic procedure, and can operate integrally by manipulating the operation module H.

The second intermediate connection part 320' may connect the operation module H and the force applying module 400 disposed at the insertion end by the medium of the intermediate connection member 105. In this case, the second intermediate connection part 320' may be provided with one second intermediate connection body 315 and a second connection end E5.

The second intermediate connection body 315 may be inserted penetrating the second middle hollow spaced apart from the first middle hollow. At this time, both ends of the second intermediate connection body 315 may be disposed at least partially outside the first module body 310.

The second connection end E5 may be detachably connected to the second engaging member 335 to be described later. The second connection end E5 may be disposed at one end of the second intermediate connection body 315, and the intermediate connection member 105 may be provided at the other end of the second intermediate connection body 315. In this case, the intermediate connection member 105 may be connected to the third operation part H30 by the medium of the lifting unit.

As exemplarily shown in the drawings, the intermediate connection member 105 may be formed to protrude from the second intermediate connection body 315 toward the rear (−Y axis direction) in parallel with the longitudinal direction (Y axis direction). In this case, the rear end of the intermediate connection member 105 may be provided with a protrusion for engagement to engage with the linear movement shaft of the lifting unit. In this case, after the intermediate connection member 105 is inserted into an engagement groove (not shown) provided at the front end of the linear movement shaft, the engagement protrusion can be engaged and secured in the engagement groove. By this, the intermediate connection member 105 and the second intermediate connection body 315 can be coupled to the lifting unit. Meanwhile, the present disclosure is not limited to this, but as another embodiment, the intermediate connection member 105 may be connected to the linear movement shaft by the medium of a connection wire (not shown).

In this case, as the user manipulates the third operation part H30 in the operation direction, the linear movement shaft and the intermediate connection member 105 connected thereto can perform a rectilinear motion in the force applying direction (−Y axis direction) by the hydraulic pressure supplied from the hydraulic pressure supply part. At the same time, the second intermediate connection body 315 and the second connection end E5 may perform a rectilinear motion in the force applying direction (−Y axis direction).

A second insertion groove 325 and a second guide projection T5 may be formed at the second connection end E5, and the second guide projection T5 may move along the second guide slit G5 provided in the first module body 310 and may guide the movement of the second intermediate connection body 315. Other specific features of the second intermediate connection part 320' and the coupling method with the second insertion end connection part 340' are the same as or similar to those of the above-described first intermediate connection part 320, so redundant descriptions thereof will be omitted.

As described above, the first intermediate connection part 320 may include two pairs of first intermediate connection bodies 311, 312, 313, and 314. In this case, for the convenience of description, the two pairs of first intermediate connection bodies 311, 312, 313, and 314 will be referred to as the first-first intermediate connection body 311, the first-second intermediate connection body 312, the first-third intermediate connection body 313, and the first-fourth intermediate connection body 314.

In this case, two pairs of first middle hollows may be formed in the first module body 310, and the first-first, first-second, first-third, and first-fourth intermediate connection bodies 311, 312, 313, and 314 may be inserted penetrating them, respectively.

The first-first, first-second, first-third, and first-fourth intermediate connection bodies 311, 312, 313, and 314 may be arranged symmetrically with each other, within the first module body 310, in the width direction (X axis direction) and/or in the height direction (Z axis direction). Specifically, the first-first intermediate connection body 311 may be arranged symmetrically with the first-second intermediate connection body 312 in the width direction (X axis direction). At this time, the first-first intermediate connection body 311 may be arranged symmetrically with the first-third intermediate connection body 313 in the height direction (Z axis direction), and the first-third intermediate connection body 313 may be arranged symmetrically with the first-fourth intermediate connection body 314 in the width direction (X axis direction). Accordingly, the first-first intermediate connection body 311 and the first-second intermediate connection body 312 can be arranged side by side in a pair on the upper side inside the first module body 310, and the first-third intermediate connection body 313 and the first-fourth intermediate connection body 314 can be arranged side by side in a pair on the lower side inside the first module body 310.

In this case, the second middle hollow may extend beyond the inner region of the first module body 310, defined by the first-first, first-second, first-third, and first-fourth intermediate connection bodies 311, 312, 313, and 314, and as a result, the second intermediate connection part 320' may be surrounded by the first-first, first-second, first-third, and first-four intermediate connection bodies 311, 312, 313, and 314 to be located in the center.

The connection ends of the first and second intermediate connection bodies 311, 312, 313, 314, and 315, that is, the first-first connection end E1, the first-second connection end E2, and the first-third connection end E3, the fnst-fourth connection end E4, and the second connection end E5 may be arranged to protrude outward from the first module body 310 towarl the insertion unit 200.

Additionally, the first connection wire 101, the second connection wire 102, the third connection wire 103, and the fourth connection wire 104 may be connected to the other ends of the first intermediate connection bodies 311, 312, 313, and 314, respectively, which are opposite to the first connection ends E1, E2, E3, and E4. And the above-described intermediate connection member 105 may be provided at the other end of the second intermediate connection body 315 opposite to the second connection end E5, so that the other ends can be connected to the lifting unit. In this case, each of the first intermediate connection bodies 311, 312, 313, and 314 may be disposed in the first module body 310 in a state of being inserted penetrating the elastic member in the form of a coil spring.

As described above, the second detachment module 300b may be provided with the second module body 330, the first insertion end connection part 340, and the second insertion end connection part 340'.

The second module body 330 may be a housing in which a first insertion end hollow and a second insertion end hollow penetrating both ends along a longitudinal direction (Y axis direction) are formed.

The first insertion end connection part 340 can transfer the force applied by the user's manipulation of the operation module H to the insertion end by the medium of the first, second, third, and fourth operation wires 201, 202, 203, and 204, so that the insertion end of the insertion unit 200 can perform a bending motion. In this case, the first insertion end connection part 340 may include two pairs of first insertion end connection bodies 341, 342, 343, and 344, which are provided with the first engaging members 331, 332, 333, and 334, respectively.

The first insertion end connection bodies 341, 342, 343, and 344 may be bars having an elongate cylindrical shape in an example. The first insertion end connection bodies 341, 342, 343, and 344 may be inserted penetrating the first insertion end hollow of the second module body 330. In this case, both ends of the first insertion end connection bodies 341, 342, 343, and 344 may be arranged protruding at least partially to the outside of the second module body 330.

Each of the first insertion end connection bodies 341, 342, 343, and 344 may have a rack gear part L on its one surface. Each of the rack gear parts L may be disposed on a surface among surfaces of the first insertion end connection body 341, 342, 343, or 344, which faces the center of the second module body 330. And, the rack gear parts L may extend along the longitudinal direction (Y axis direction) of the first insertion end connection bodies 341, 342, 343, and 344.

The first engaging members 331, 332, 333, and 334 can be inserted into the aforementioned first insertion grooves 321, 322, 323, and 324 of the first connection ends E1, E2, E3, and E4, and can be detachably coupled thereto.

The first engaging members 331, 332, 333, and 334 may be disposed at one ends of the first insertion end connection bodies 341, 342, 343, and 344, and the one ends of the first insertion end connection bodies 341, 342, 343, and 344 may be ends facing the operation unit 100. In this case, one ends of the first, second, third, and fourth operation wires 201, 202, 203, and 204 can be connected to the other ends of the first insertion end connection bodies 341, 342, 343, and 344, and the other ends of the first, second, third, and fourth operation wires 201, 202, 203, and 204 can be connected to the inside of the insertion ends.

At this time, the first engaging members 331, 332, 333, and 334 may be formed in a protruding length similar to the depth of the concaves inward in the longitudinal direction of the first insertion grooves 321, 322, 323, and 324, preferably in a shorter protruding length. Accordingly, when the first engaging members 331, 332, 333, and 334 are inserted into the first insertion grooves 321, 322, 323, and 324, a predetermined clearance may exist between the first engaging members 331, 332, 333, and 334 and the first insertion grooves 321, 322, 323, and 324.

The second insertion end connection part 340' can transfer the force applied by the user manipulating the third operation part H30 by the medium of the fifth operation wire 205 to the force applying module 400, so that the force applying module 400 can rotate. In this case, the second insertion end connection part 340' may include one second insertion end connection body 345, a curved connection member 346, and a second engaging member 335.

The second insertion end connection body 345 may be inserted penetrating the second insertion end hollow spaced apart from the first insertion end hollow. In this case, both ends of the second insertion end connection body 345 may be disposed at least partially outside the second module body 330.

The curved connection member 346 may be disposed between the second insertion end connection body 345 and the force applying module 400, and may have a hollow formed therein for accommodating the operation wire 205. The operation wire 205 may be disposed in the inner hollow of the curved connection member 346, and extend toward the force applying module 400 from the second insertion end connection body 345. In this case, one end of the operation wire 205 can be connected to the second insertion end connection body 345, and the other end of the operation wire 205 can be connected to the force applying module 400.

The curved connection member 346 may have a curved part curved with respect to the longitudinal direction (Y axis direction) of the second insertion end connection part 340'. Through this curved part, the disposal state such as the bending direction, bending degree, and the like of the operation wire 205 disposed inside the inner hollow of the curved connection member 346 can be adjusted.

Specifically, the second operation wire 205 may have one end connected to the second insertion end connection body

345 and the other end extending toward the insertion end. In this case, a part between the aforementioned one end and the other end of the second operation wire 205 can be bent and extended along the curved connection member 346. Accordingly, among the entire length of the second operation wire 205, the length extending past the curved connection member 346 may be disposed extending toward the insertion end inside the insertion unit 200 in the longitudinal direction (Y axis direction) to pass through the center of the insertion unit 200.

Additionally, the second insertion end connection part 340' can be placed without affecting the second insertion end connection part 340' disposed in a straight line within the limited space inside the second module body 330 through the curved connection member 346, so that the space utilization can be improved.

The second engaging member 335 may be inserted into the second insertion groove 325 of the second connection end E5 and detachably coupled thereto. The second engaging member 335 may be formed protruding outward in the longitudinal direction (–Y axis direction) at the opposite end of the curved connection member 346 among both ends of the second insertion end connection body 345. In this case, one end of the operation wire 205 can be connected to the other end of the second insertion end connection body 345, and the other end of the fifth operation wire 205 can be connected to the force applying module 400.

In this case, as the user manipulates the third operation part H30 in the operation direction, the linear movement shaft and the intermediate connection member 105 connected thereto and the second intermediate connection body 315 can perform a rectilinear motion in the force applying direction (–Y axis direction) by the hydraulic pressure supplied from the hydraulic pressure supply part.

In this case, a second insertion groove 325 and a second guide projection T5 can be formed at the second connection end E5, and the second guide projection T5 can move along the second guide slit G5 provided in the second module body 330, and can guide the movement of the second intermediate connection body 315. Other specific features of the second intermediate connection part 320' and the coupling method with the second insertion end connection part 340' and the operation manner after the coupling are the same as or similar to those of the above-described first intermediate connection part 320, so redundant descriptions thereof will be omitted.

As described above, the first insertion end connection part 340 may include two pairs of first insertion end connection bodies 341, 342, 343, and 344. In this case, for the convenience of description, the two pairs of first insertion end connection bodies will be referred to as the first-first insertion end connection body 341, the first-second insertion end connection body 342, the first-third insertion end connection body 343, and the first-fourth insertion end connection body 344.

In this case, two pairs of first insertion end hollows may be formed in the second module body 330, and the first-first, first-second, first-third, and first-fourth insertion end connection bodies 341, 342, 343, and 344 may be inserted penetrating these two pairs of first insertion end hollows, respectively.

The first-first, first-second, first-third, and first-fourth insertion end connection bodies 341, 342, 343, and 344 may be arranged symmetrically with each other in the width direction (X axis direction) and/or the height direction (Z axis direction) in the second module body 330.

Specifically, the first-first insertion end connection body 341 may be arranged symmetrically with the first-second insertion end connection body 342 in the width direction (X axis direction). Accordingly, the rack gear part L of the first-first insertion end connection body 341 and the rack gear part L of the first-second insertion end connection body 342 can be arranged to face each other.

Additionally, the first-first insertion end connection body 341 may be arranged symmetrically with the first-third insertion end connection body 343 in the height direction (Z axis direction), and the first-third insertion end connection body 343 may be arranged symmetrically with the first-fourth insertion end connection body 344 in the width direction (X axis direction). Accordingly, the third rack gear part L of the first-third insertion end connection body 343 and the fourth rack gear part L of the first-fourth insertion end connection body 344 may be arranged to face each other.

Accordingly, the first-first insertion end connection body 341 and the first-second insertion end connection body 342 can be arranged side by side in a pair on the upper side inside the second module body 330, and the first-third insertion end connection body 343 and the first-fourth insertion end connection body 344 can be arranged side by side in a pair on the lower side inside the second module body 330.

In this case, as described above, the second insertion end connection part 340' may be disposed in a region defined by being surrounded by the first-first, first-second, first-third, and first-fourth insertion end connection bodies 341, 342, 343, and 344 in the second module body 330. In this case, the second insertion end connection body 345, in one embodiment, can extend through the middle of the first-first, first-second, first-third, and first-fourth insertion end connection bodies 341, 342, 343, and 344.

In the above case, the second module body 330 may be provided with a pinion gear unit P. In this case, the pinion gear unit P may include a first pinion gear P10 (FIGS. 5 and 6), and a second pinion gear P20 (see FIGS. 5 and 6).

The first pinion gear P10 may be disposed between the first-first insertion end connection body 341 and the first-second insertion end connection body 342, so that it can be meshed with the first rack gear part L of the first-first insertion end connection body 341 and the second rack gear part L of the first-second insertion end connection body 342 at the same time. In this meshed state, the first pinion gear P10 may rotate around the first central axle part perpendicular to the longitudinal direction (Y axis direction) according to the user's manipulation of the operation module H.

The second pinion gear P20 may be disposed between the first-third insertion end connection body 343 and the first-fourth insertion end connection body 344, so that it can be meshed with the third rack gear part L of the first-third insertion end connection body 343 and the fourth rack gear part L of the first-fourth insertion end connection body 344 at the same time. In this meshed state, the second pinion gear P20 may rotate around the second central axle part perpendicular to the longitudinal direction (Y axis direction) according to the user's manipulation of the operation module H.

The second central axle part may be disposed on the same line as the first central axle part, but may be configured to be separated from each other and independently rotatable. Accordingly, while the first pinion gear P10 and the second pinion gear P20 rotate around the first central axle part or the second central axle part, they can avoid interfering (or hindering) each other's rotational movements.

The second module body 330 may be provided with a guide hole (not shown) which is formed penetrating in the longitudinal direction (Y axis direction) while passing past the center of a region surrounded by the first-first, first-second, first-third, and first-fourth insertion end connection bodies 341, 342, 343, and 344. In this regard, the guide hole may be disposed between the first pinion gear and the second pinion gear so as not to interfere with rotation of the pinion gears. In this case, the second insertion end connection body 345 can be disposed inside the above-described guide hole, and can perform reciprocating rectilinear motion in parallel with the longitudinal direction (Y axis) inside the guide hole.

The second module body 330 may be provided with straight line guide slits G extending along the longitudinal direction (Y axis direction) on its upper and lower surfaces. The straight line guide slits G may include a pair of 'upper surface straight line guide slits' provided on the upper surface of the second module body 330 to face the first-first insertion end connection body 341 and the first-second insertion end connection body 342, respectively, and a pair of 'lower surface straight line guide slits' provided on the lower surface of the second module body 330 to face the first-third insertion end connection body 343 and the first-fourth insertion end connection body 344, respectively.

In this case, the first-first insertion end connection body 341 and the first-second insertion end connection body 342 may each be provided with 'upper surface guide protruding members I' extending upward and inserted into the supper surface straight line guide slits G. And the first-third insertion end connection body 343 and the first-fourth insertion end connection body 344 may each be provided with 'lower surface guide protruding members I' extending downward and inserted into the lower surface straight line guide slits G. In this case, respective guide protruding members I can guide the reciprocating rectilinear motion of the first insertion end connection bodies 341, 342, 343, and 344 by moving along the corresponding linear guide slits G.

At one end of each of the first-first, first-second, first-third, and first-fourth insertion end connection bodies 341, 342, 343, and 344, the first-first engaging member 331, the first-second engaging member 332, the first-third engaging member 333, or the first-fourth engaging member 334 may be provided. And, to the other end of each of the first-first, first-second, first-third, and first-fourth insertion end connection bodies 341, 342, 343, and 344, the first operation wire 201, the second operation wire 202, the third operation wire 203, or the fourth operation wire 204 may be connected.

Figure 5:
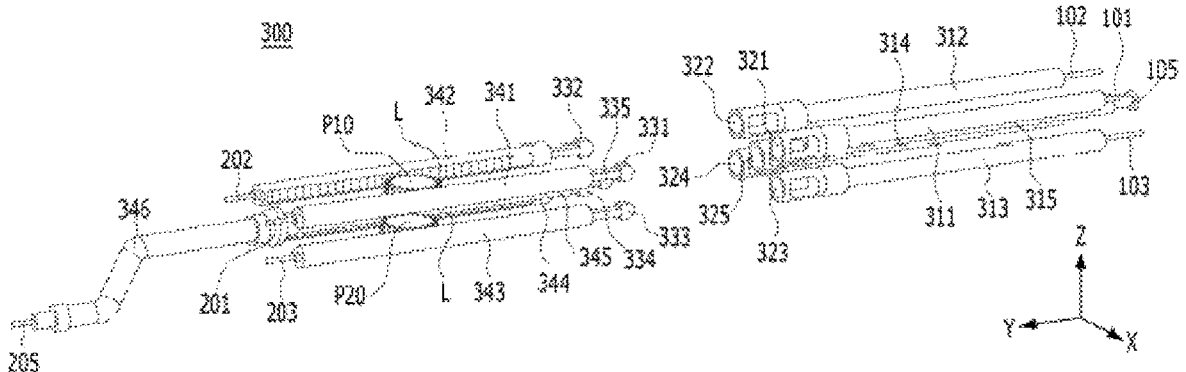
FIG. 5 is a perspective view showing the inside of the first detachment module and the second detachment module in a state before they are coupled in FIG. 3.
Figure 6:
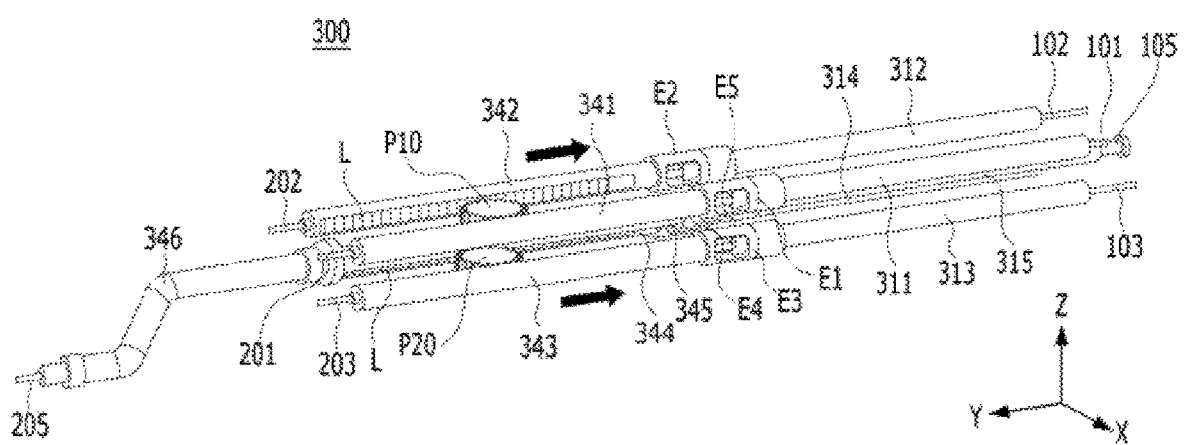
FIG. 6 is a perspective view showing the inside of the first detachment module and the second detachment module in a coupled state of FIG. 4.

FIG. 5 is a perspective view showing the inside of the first detachment module and the second detachment module in a state before they are coupled in FIG. 3. FIG. 6 is a perspective view showing the inside of the first detachment module and the second detachment module in a coupled state of FIG. 4.

Referring to FIGS. 5 and 6, a method in which the operation unit 100 and the insertion unit 200 are coupled to each other may be as follows.

First, the first coupling end of the operation unit 100 and the second coupling end of the insertion unit 200 may be disposed to face each other. At this time, before coupling, the first coupling end of the operation unit 100 may be in a 'parallel-aligned state' with the second coupling end of the insertion unit 200.

Here, when viewing the detachable endoscope 10 from above based on the Z axis of the drawing, the 'parallel-aligned state' may mean a state in which the virtual first reference line connecting the first-first connection end E1 and the first-second connection end E2 [and connecting the first-third connection end E3 and the first-fourth connection end E4] provided in the operation unit 100 is parallel to the virtual second reference line connecting one end of the first-first insertion end connection body 341 and one end of the first-second insertion end connection body 342 [and connecting one end of the first-third insertion end connection body 343 and one end of the first-fourth insertion end connection body 344] provided in the insertion unit 200.

Next, the operation unit 100 and the insertion unit 200 can move in a direction parallel to the longitudinal direction (Y axis direction) and approaching each other (hereinafter, referred to as a coupling direction). Accordingly, the first-first engaging member 331, the first-second engaging member 332, the first-third engaging member 333, and the first-fourth engaging member 334 of the insertion unit 200 can be inserted into the first-first insertion groove 321 of the first-first connection end E1, the first-second insertion groove 322 of the first-second connection end E2, the first-third insertion groove 323 of the first-third connection end E3, and the first-fourth insertion groove 324 of the first-fourth connection end E4. At this time, the second engaging member 335 of the second insertion end connection part 340' can be inserted into the second insertion groove 325 provided in the second connection end E5 of the second intermediate connection part 320'.

Next, when the first and second intermediate connection part 320 and 320' move backward (−Y axis direction) by the user's manipulation of the operation module H, the first and second connection ends E1, E2, E3, E4, and E5 and the first and second intermediate connection bodies 311, 312, 313, 314, and 315 may move backward (−Y axis direction) while being rotated by the first and second guide projections T1, T2, T3, T4, and T5 and the first and second guide slits G1, G2, G3, G4, and G5. With this, the first and second engaging members 331, 332, 333, 334, and 335 may be secured to one ends of the first and second insertion grooves 321, 322, 323, 324, and 325 in the engaged state, so that the insertion unit 200 and the operation unit 100 can be coupled with each other. In this regard, the specific combination method will be described in detail below.

Figure 7A:
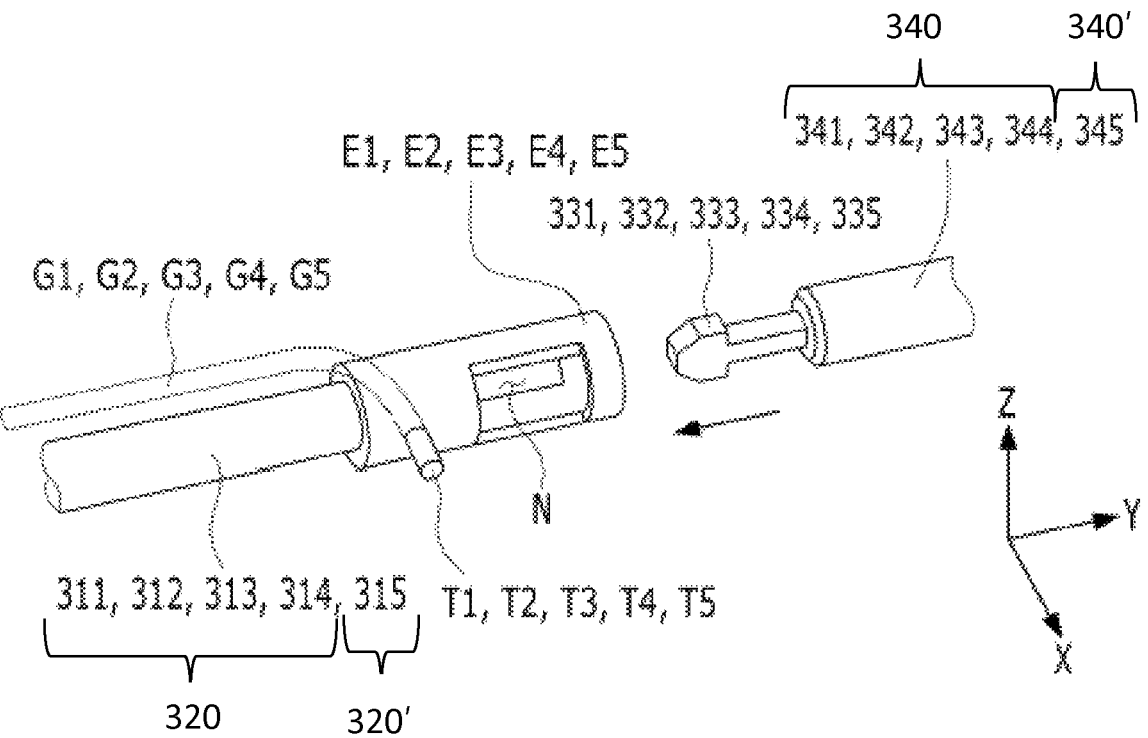
FIG. 7A is a perspective view showing a state before the intermediate connection part and the insertion end connection part provided in the detachable endoscope according to an embodiment of the present disclosure are coupled to each other.
Figure 7B:
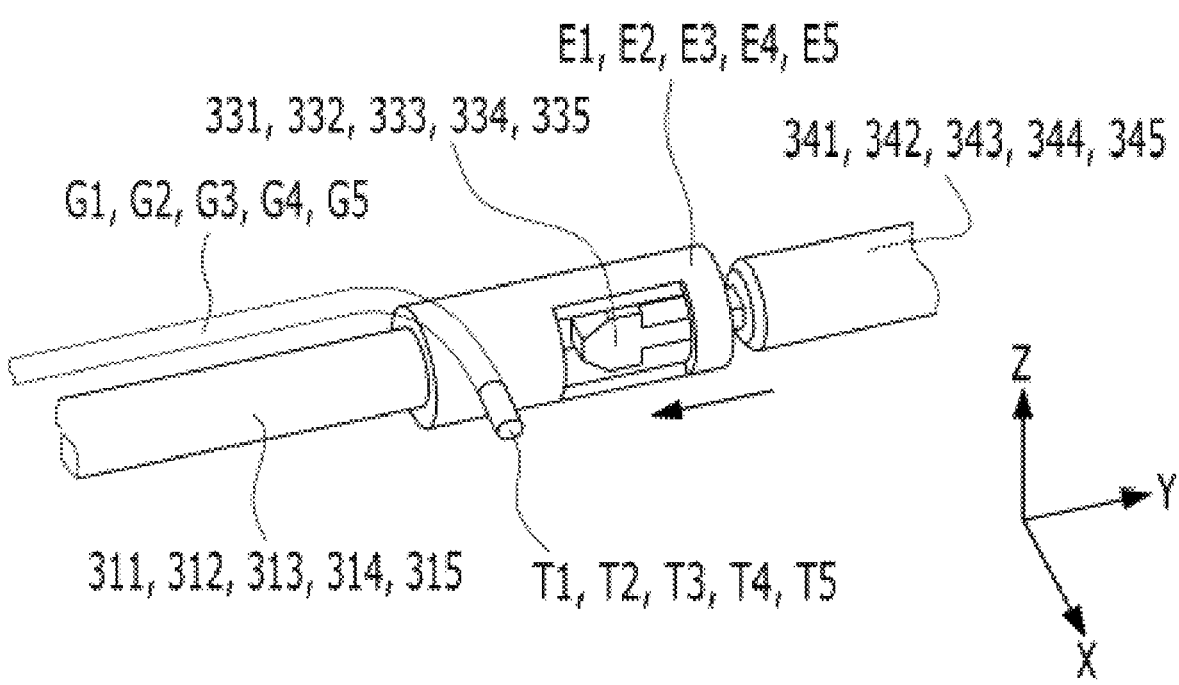
FIGS. 7B and 7C are perspective views showing states before the coupling of the intermediate connection part and the insertion end connection part is completed.
Figure 7C:
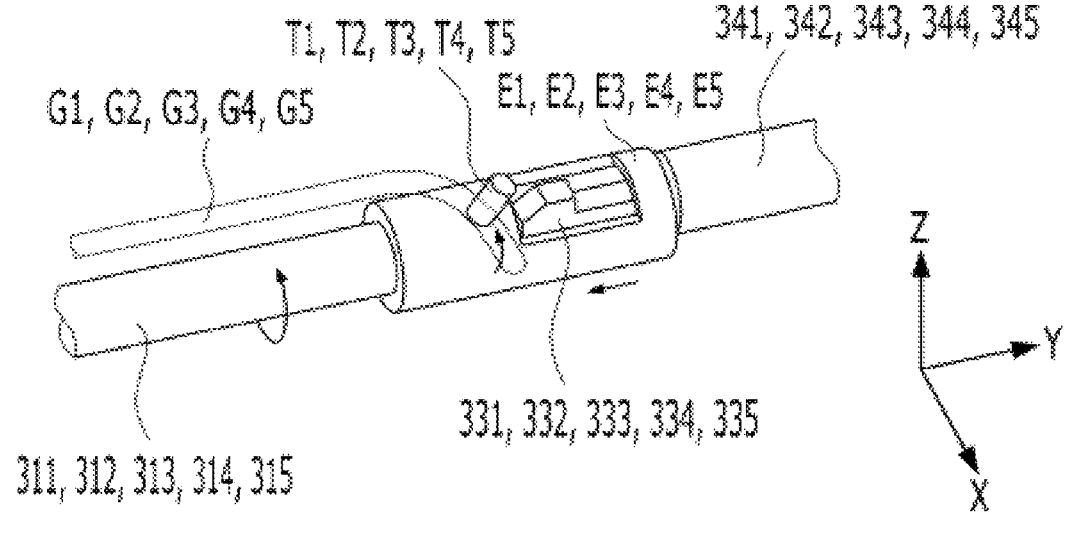
Figure 7D:
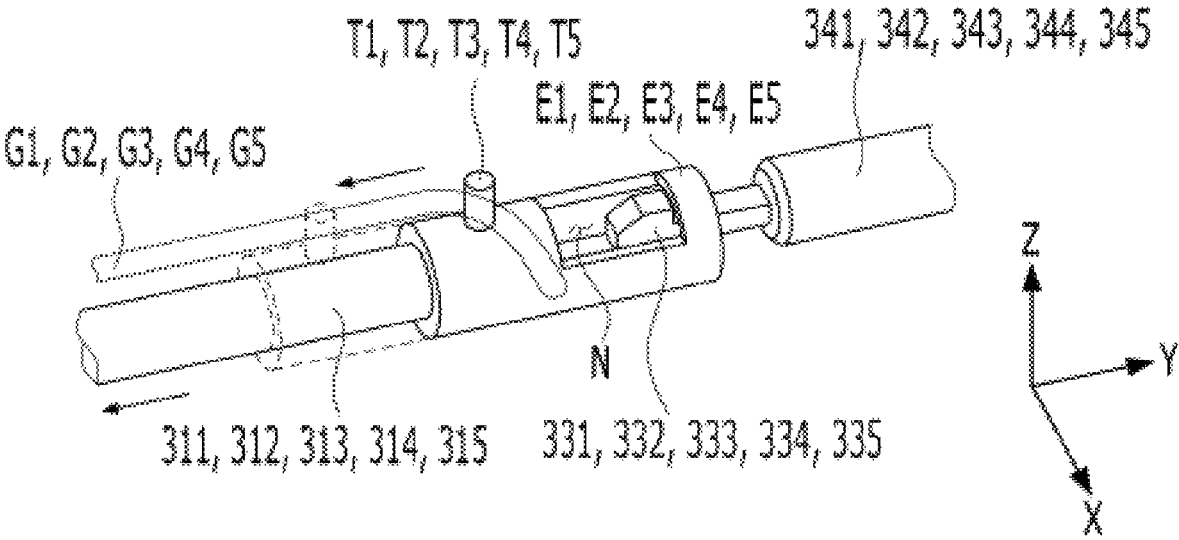
FIG. 7D is a perspective view showing a state in which the intermediate connection part and the insertion end connection part are coupled.
Figure 8:
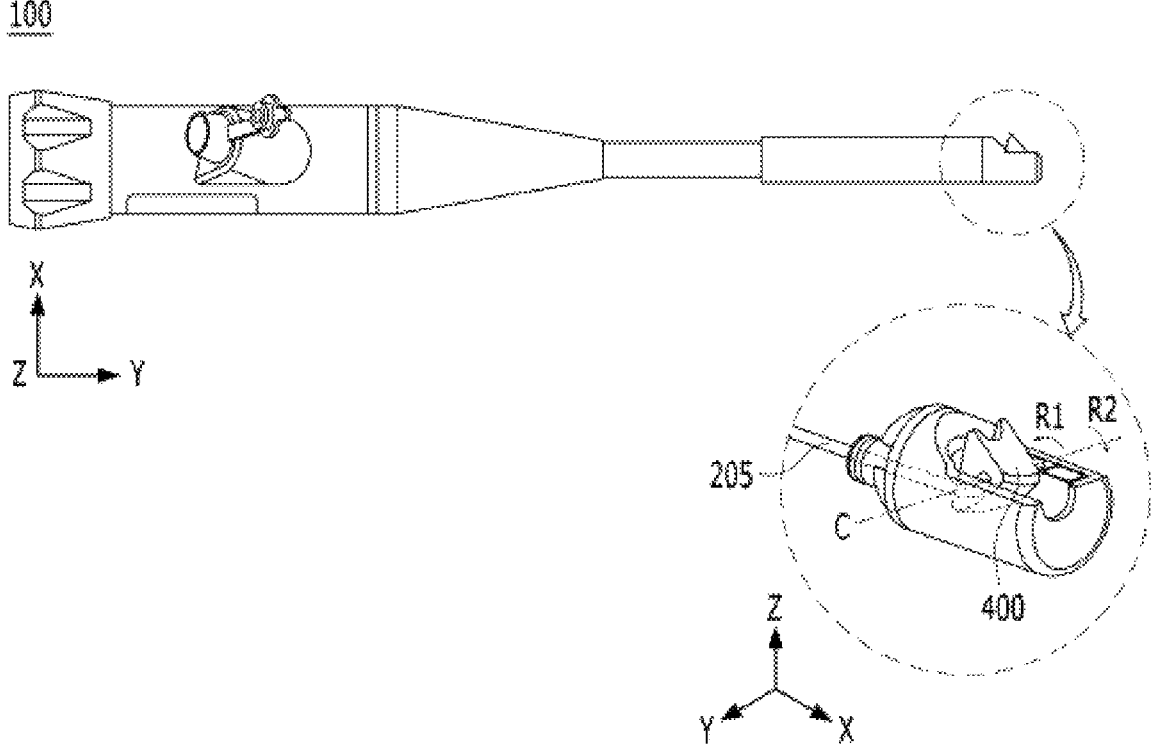
FIG. 8 is a plan view showing an insertion unit according to an embodiment of the present disclosure.

FIG. 7A is a perspective view showing a state before the intermediate connection part and the insertion end connection part provided in the detachable endoscope according to an embodiment of the present disclosure are coupled to each other. FIGS. 7B and 7C are perspective views showing states before the coupling of the intermediate connection part and the insertion end connection part is completed. FIG. 7D is a perspective view showing a state in which the intermediate connection part and the insertion end connection part are coupled.

Referring to FIGS. 7A to 7D, a method for coupling the first intermediate connection part 320 or the second intermediate connection part 320' provided in the operation unit 100 with the first insertion end connection part 340 or the second insertion end connection part 340' provided in the insertion unit 200 may be as follows.

First, as described above, when the operation unit 100 and the insertion unit 200 in a state before coupling are disposed facing each other, the first and second intermediate connection parts 320 and 320' and the first and second insertion end connection parts 340 and 340' may be disposed facing each other. At this time, in a state where the first and second connection ends E1, E2, E3, E4, and E5 face the first and second engaging members 331, 332, 333, 334, and 335 each other, the first and second intermediate connection bodies 311, 312, 313, 314, and 315 may be arranged on the same line as the first and second insertion end connection bodies 341, 342, 343, 344, and 345 in the longitudinal direction (Y axis direction) (see FIG. 7A).

Next, the operation unit 100 and the insertion unit 200 may be moved so as to come closer along the coupling direction by the user. In this case, the first and second engaging members 331, 332, 333, 334, and 345 can be inserted into the first and second insertion grooves 321, 322, 323, 324, and 325 provided at the first and second connection ends E1, E2, E3, E4, and E5.

At this time, the first and second engaging members 331, 332, 333, 334, and 335 may be provided with an 'engaging projection' protruding toward the outer side of the radial direction of the first and second engaging members 331, 332, 333, 334, and 335 at their front ends. When the first and second engaging members 331, 332, 333, 334, and 335 are inserted into the first and second insertion grooves 321, 322, 323, 324, and 325, the engaging projections may be accommodated in the first and second insertion grooves 321, 322, 323, 324, and 325 (see FIG. 7B).

Next, as the operation unit 100 and the insertion unit 200 move further along the coupling direction (Y axis direction), the front ends of the first and second insertion end connection bodies 341, 342, 343, 344, and 345 may come into contact with the first and second connection ends E1, E2, E3, E4, and E5. At this time, the first and second engaging members 331, 332, 333, 334, and 335 are formed in a length shorter than or equal to the depth of the first and second insertion grooves 321, 322, 323, 324, and 325, so the first and second engaging members can avoid interference in contact between the first and second insertion end connection bodies 341, 342, 343, 344, and 345, and the first and second connection ends E1, E2, E3, E4, and E5.

Next, the user may operate a locking part 200a provided at the second coupling end of the insertion unit 200 to couple and secure the insertion unit 200 to the operation unit 100. As an example, the locking part 200a may be rotatably installed at the second coupling end, and the first coupling end of the operation unit 100 may be inserted into this locking unit 200a. In this case, as the user rotates the locking part 200a in one direction, the locking part 200a and the first coupling end may be coupled in a screw connection method and secured together.

In this regard, when the locking part 200a is rotated, the first and second insertion end connection bodies 341, 342, 343, 344, and 345 are further moved in the coupling direction (–Y axis direction) in a state of being in contact with the first and second connection ends E1, E2, E3, E4, and E5, so that they can press the first and second connection ends E1, E2, E3, E4, and E5 and the first and second intermediate connection bodies 311, 312, 313, 314, and 315 backward (–Y axis direction). With this, the first and second guide projections T1, T2, T3, T4, and T5 move backward (–Y axis direction) while rotating along the 'curved line parts' of the first and second guide slits G1, G2, G3, G4, and G5, and as a result, the first and second connection ends E1, E2, E3, E4, and E5 and the first and second intermediate connection bodies 311, 312, 313, 314, and 315 can be rotated around the longitudinal direction (Y axis direction).

By this rotation, in a state where the first and second engaging members 331, 332, 333, 334, and 335 are accommodated in the first and second insertion grooves 321, 322, 323, 324, and 325, the engaging projections can protrude to the outside of the first and second insertion grooves 321, 322, 323, 324, and 325 through the penetration part N to be in a non-separable state (primary coupled state) (see FIG. 7C).

Next, in the primary coupled state, by the user's manipulation of the operation module H, the first and second intermediate connection part 320 and 320' can be pulled backward (–Y axis direction). In this case, the first and second guide projections T1, T2, T3, T4, and T5 pass through the 'curved line parts' of the first and second guide slits G1, G2, G3, G4, and G5 and move backward (–Y axis direction) along the 'straight line parts,' and accordingly, the engaging projections of the first and second engaging members 331, 332, 333, 334, and 335 protruding outward through the penetration part N can be in the engaged state at the inner ends of the first and second insertion grooves 321, 322, 323, 324, and 325. As a result, the first and second intermediate connection parts 320 and 320' and the first and second insertion end connection parts 340 and 340' may be coupled to become a non-separable state (secondary coupled state)(see FIG. 7D).

Thereafter, in the 'secondary coupled state', by the user's manipulation of the operation module H, the first intermediate connection part 320 and the first insertion end connection part 340 can operate to perform reciprocating rectilinear motion integrally, and the second intermediate connection part 320' and the second insertion end connection part 340' can operate to perform reciprocating rectilinear motion integrally.

Meanwhile, when removal or replacement of the insertion unit 200 is required, the insertion unit 200 may be separated from the operation unit 100 by a process as follows.

First, reference points (not shown) provided respectively on the first operation part H10, the second operation part H20, and the third operation part H30 may be aligned in a line. In this way, when the first, second, and third operation parts H10, H20, and H30 are aligned along the reference points, the operation unit 100 and the insertion unit 200 can again be in a 'parallel-aligned state' as described above.

Next, the locking state may be released by rotating the locking part 200a of the insertion unit 200 in a direction opposite to the locking direction. After the unlocking of the locking part 200a is completed, the user may separate the insertion unit 200 by moving it away from the operation unit 100 in a direction opposite to the coupling direction. Thereafter, the replacement of the insertion unit 200 may be completed by coupling another insertion unit as a replacement to the operation unit 100 through the same or similar method as described above.

Regarding the operation method of the detachable endoscope 10 according to the above-described present disclosure, in the case where the insertion unit 200 and the operation unit 100 are assembled in the 'second coupled state', by the user's manipulation of the first operation part H10 or the second operation part H20, the first intermediate connection part 320 performs reciprocating rectilinear motion through the lower sprocket and the upper sprocket, and the lower chain and upper chain respectively connected thereto, and at this time, the first insertion end connection part 340 can perform reciprocating rectilinear motion integrally with the first intermediate connection part 320 while being coupled with it through the first engaging members 331, 332, 333, and 334 and the first insertion grooves 321, 322, 323, and 324, respectively.

Additionally, in the 'second coupled state', the hydraulic pressure supply part supplies hydraulic pressure to the linear movement shaft or removes the supplied hydraulic pressure by the user's manipulation of the third operation part H30, and thus the second intermediate connection part 320' and the second insertion end connection part 340' which are coupled through the second engaging member 335 and the second insertion groove 325 can perform reciprocating rectilinear motion integrally.

In this case, the first detachment module 300*a* may be connected to the operation module H by the medium of the lower sprocket and the upper sprocket rotated in forward/backward directions by the first and second operation parts H10 and H20, the lower chain and the upper chain connected thereto to be wound around them, and the first, second, third and fourth connection wires 101, 102, 103 and 104 connected to both ends of the chains. Additionally, the first detachment module 300*a* may be connected to the operation module H by the medium of a hydraulic pressure supply part and a linear movement shaft that perform reciprocating rectilinear motion forward/rearward by the third operation part H30, and the intermediate connection member 105 coupled to them.

The first and second connection wires 101 and 102 connected to both ends of the upper chain connected to the upper sprocket operate in linkage with the first and second operation wires 201 and 202 disposed side by side in a pair on the upper side of the inside of the insertion unit 200 based on the drawing, so that the first and second connection wires can bend the insertion end of the insertion unit 200 in the left and right directions.

Contrarily, the third and fourth connection wires 103 and 104 connected to both ends of the lower chain connected to the lower sprocket operate in linkage with the third and fourth operation wires 203 and 204 disposed side by side in a pair on the lower side of the inside of the insertion unit 200 based on the drawing, so that the third and fourth connection wires can bend the insertion end of the insertion unit 200 in the up and down directions. However, the present disclosure is not limited to this, and bending manipulations in the up and down directions and the left and right directions may be reversed depending on the design of the endoscope 10.

The intermediate connection member 105 connected to the hydraulic pressure supply part and the linear movement shaft is surrounded by the first, second, third and fourth connection wires 101, 102, 103 and 104 and is disposed within a defined space, so that it can operate in linkage with the fifth operation wire 205 to cause the force applying module 400 to pivot. In this case, the fifth operation wire 205 may be disposed in a space surrounded by the first, second, third, and fourth operation wires 201, 202, 203, and 204.

In the detachable endoscope 10 according to the embodiments of the present disclosure, the insertion unit 200 intended to be inserted into the human body is configured to be detachable from the operation unit 100, so that the internal contamination of the endoscope 10 can be prevented and parts can be easily replaced and cleaned. Additionally, in the course of coupling, without the use of a separate engaging or locking structure, it is possible to realize simple and easy assembly and disassembly of the insertion unit 200.

The afore-mentioned description of the disclosure is just an example, and a person having ordinary skill in the art may understand that it can be easily modified into other specific configuration without changing the technical spirit or essential features of the disclosure. Thus, the embodiments described above should be construed as being illustrative in every respect and not restrictive. For example, the respective components described as a singular form may be implemented in a distributed form, and likewise the respective components described as a distributed form may be implemented in a combined form.

The scope of the present disclosure is represented by the following claims, and all modifications and changes derived from the meaning and scope of the claims and equivalent concepts thereof should be interpreted as being included in the scope of the present disclosure.

REFERENCE SIGN LIST

10: Detachable endoscope
100: Operation unit
200: Insertion unit
300: Detachment unit
400: Force applying module
H: Operation module

What is claimed is:

1. A detachable endoscope for a duodenum, comprising:
an insertion unit having one end configured to be inserted into a body, the insertion unit including a force applying module disposed on the one end, the force applying module having a pivotal axis, the force applying module being pivotable around the pivotal axis;
an operation unit having a distal end coupled to another end of the insertion unit, the operation unit having an operation module which includes at least one knob, and the operation unit being configured to operate the one end of the insertion unit to perform a bending motion of the insertion unit by the operation module; and
a detachment unit including a first detachment module disposed within the operation unit, and a second detachment module disposed within the insertion unit, the first detachment module and the second detachment module being configured to be detachably coupled to each other,
wherein the first detachment module includes:
a first module body;
a first intermediate connection part disposed within the first module body and configured to receive a force from the operation module; and
a second intermediate connection part disposed within the first module body and configured to receive the force from the operation module, the second intermediate connection part having a distal end and a proximal end, and
wherein the second detachment module includes:
a second module body;
a first insertion end connection part disposed within the second module body, configured to be detachably connected to the first intermediate connection part, and connected to a first operation wire configured to transfer the force applied by the operation module to the one end of the insertion unit; and
a second insertion end connection part disposed within the second module body and having a distal end connected to a second operation wire configured to transfer the force applied by the operation module to the force applying module,
wherein the first intermediate connection part includes two pairs of first intermediate connection bodies, which are spaced apart from each other along an inner circumference of the first module body, and the second intermediate connection part extends through a center of the two pairs of the first intermediate connection bodies, and
wherein the first insertion end connection part includes two pairs of first insertion end connection bodies corresponding to the first intermediate connection bodies, respectively, and the two pairs of the first insertion end connection bodies are spaced apart from each other along an inner circumference of the second module body, and the second insertion end connection part extends through a center of the two pairs of the first insertion end connection bodies, wherein the insertion unit further includes:

first and second rack gear parts respectively disposed on a first pair of the two pairs of first insertion end connection bodies;

third and fourth rack gear parts respectively disposed on a second pair of the two pairs of first insertion end connection bodies;

a first pinion gear configured to mesh with the first and second rack gear parts;

a second pinion gear configured to mesh with the third and fourth rack gear parts; and a guide hole arranged between the first and second pinion gears, the second insertion end connection part extending within the guide hole to reciprocate rectilinearly in the guide hole.

2. The detachable endoscope for a duodenum of claim 1, wherein each of the first intermediate connection part and the second intermediate connection part includes an insertion groove defined concavely inward in a longitudinal direction at one end of each of the first intermediate connection part and the second intermediate connection part, and wherein each of the first insertion end connection part and the second insertion end connection part includes an engaging member protruding outward in the longitudinal direction from one end of each of the first insertion end connection part and the second insertion end connection part, the engaging member being configured to be detachably inserted into and coupled to the insertion groove.

3. The detachable endoscope for a duodenum of claim 2, wherein the engaging member protrudes in a length shorter than a concave depth of the insertion groove.

4. The detachable endoscope for a duodenum of claim 1, wherein the second insertion end connection part is connected to the force applying module by the second operation wire, and wherein when the first detachment module and the second detachment module are coupled to each other, the force applying module is configured to be operated to rotate about a rotational axle perpendicular to a longitudinal direction of the insertion unit by the operation module.

5. The detachable endoscope for a duodenum of claim 4, wherein the second insertion end connection part includes a curved connection member extending toward the force applying module and at least partially curved with respect to a longitudinal direction of the second insertion end connection part.

\* \* \* \* \*